United States Patent [19]

Yahata

[11] 4,337,767
[45] Jul. 6, 1982

[54] DISPOSABLE ANESTHESIA MASK COVER

[76] Inventor: James I. Yahata, 20 Lee Ter., Short Hills, N.J. 07078

[21] Appl. No.: 225,210

[22] Filed: Jan. 15, 1981

[51] Int. Cl.³ .............................................. A61M 17/02
[52] U.S. Cl. ........................... 128/206.28; 128/206.26; 128/909
[58] Field of Search ...................... 128/203.28, 205.25, 128/206.21, 206.24, 206.26, 206.28, 207.13, 909

[56] References Cited

U.S. PATENT DOCUMENTS

| | | | |
|---|---|---|---|
| Re. 29,613 | 4/1978 | Kropfhammer | 128/909 X |
| 1,416,275 | 5/1922 | Freedman | 128/909 |
| 1,775,986 | 9/1930 | Class | 128/909 |
| 2,127,136 | 8/1938 | Pobirs | 128/909 |

FOREIGN PATENT DOCUMENTS 162526  5/1921  United Kingdom ................ 128/909

Primary Examiner—Henry J. Recla
Attorney, Agent, or Firm—Hopgood, Calimafde, Kalil, Blaustein & Judlowe

[57] ABSTRACT

A disposable cover for an anesthesia mask is herein described as comprising a composite member having a pliable portion surrounding a central relatively rigid portion. The pliable portion may consist of rubber, plastic or paper and is formed with an elastomeric periphery for securing the cover over an anesthesia mask. The relatively rigid central portion may be of a stiff rubber, plastic or paper and be formed with a central cylindrical projection which frictionally engages within the gas inlet of the mask.

5 Claims, 5 Drawing Figures

DISPOSABLE ANESTHESIA MASK COVER

BACKGROUND OF THE INVENTION

The present invention relates to anesthesia masks and more particularly relates to a disposable cover for use in association with such masks.

For years the medical profession has been using compliant masks for administering gaseous anesthesia to patients. Such masks are generally formed of a relatively rigid rubber and have cushioned edges about the periphery thereof for both the purpose of patient comfort and the purpose of insuring that the mask may be compliantly pressed against the nose and mouth area of a patient with airtight contact.

Such masks adequately perform the intended function; however, they may become a source of contamination and cause the transmission of an infection of one patient to another patient who subsequently uses the mask.

The existing anesthesia masks are very costly and because of the great number of masks required to accommodate the many patients treated in today's hospitals, the use of these masks becomes a relatively significant expense to hospitals which remove a mask after it's been used for cleaning and disinfecting.

However, these masks tend to deteriorate after repeated cleaning with special solutions or with gas sterilization materials.

Furthermore, the time and cost of labor for such cleaning and sterilization processes are factors which hospitals would like to eliminate if it were possible to do so safely.

As a result of the problems presented by such existing masks, disposable anesthesia masks have been provided to eliminate the necessity for cleaning and sterilization, for the patient who is known to have a contagious disease. However, such disposable masks tend to be too expensive for one-time use, are difficult to use during a long operative procedure and typically will not properly fit over a patient's face.

It is therefore an object of the present invention to provide a device which permits the use of the existing anesthesia mask which does properly fit on a patient's face and which may be used for any operative procedure while eliminating the contamination and infection transmission problems associated therewith.

It is another object of the present invention to provide a device which permits the anesthesiologist to leave the anesthesia mask connected to the anesthesia apparatus after use so that only a disposable mask cover need be removed and a new cover put in place.

It is still a further object of the present invention to provide a disposable anesthesia mask cover which would result in economic savings to a hospital while eliminating the transmission of infectious material.

At least some of the above-cited objects are achieved by the provision of a composite anesthesia mask cover having a relatively rigid central portion generally shaped in the form of the inside surface of an anesthesia mask and surrounded by a pliable portion for covering the cushioned periphery of the mask. The outermost periphery of the pliable portion may be provided with an elastomeric device for snuggly holding the pliable portion of the cover over the mask while the relatively rigid portion is held within the mask by means of a cylindrical projection which frictionally engages and is thereby held within the gas inlet of the mask.

THE DRAWINGS

While the specification concludes with claims which particularly point out that which the applicant considers to be his invention, the following detailed description may be best understood by reference to the accompanying drawings in which:

DETAILED DESCRIPTION

Figure 1:
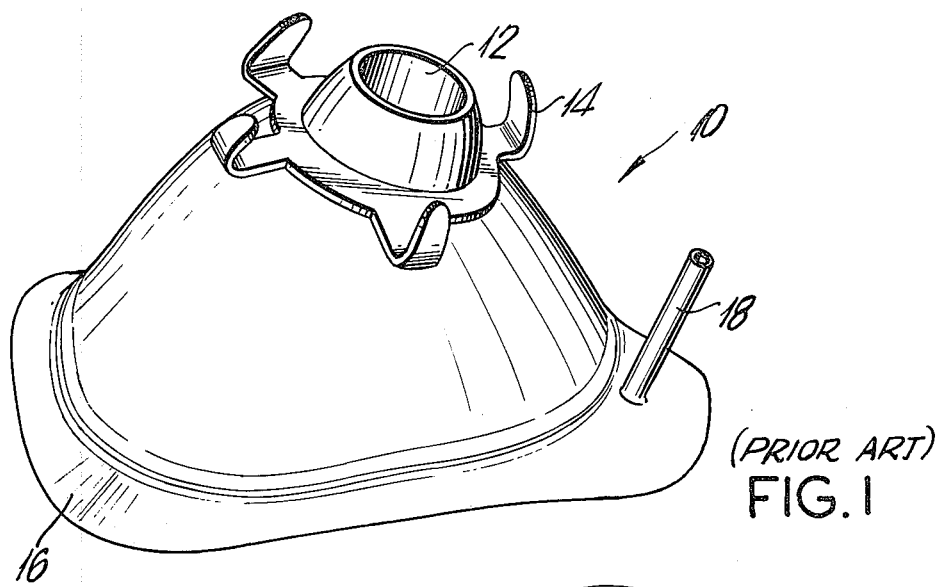
FIG. 1 is a perspective view of a conventional anesthesia mask.

Referring now to the drawings, FIG. 1 shows a conventional anesthesia mask comprising a generally cone-shaped body 10 having an anesthesia gas inlet opening 12 surrounded by a clamp 14 for attaching the mask to head straps.

The generally conical body 10 is surrounded at its periphery 16 with a cushion-like lip which typically may be inflated to a low pressure by the application of air through the valve 18.

In operation, the anesthesia gas inlet 12 is attached to an anesthesia apparatus and the overall mask is firmly pressed over the nose and mouth of a patient who is to undergo operative procedures. The cushion-like lip 16 provides both for the comfort of the patient and insures that the peripheral lips of the mask will comply with the facial contours of the patient so as to keep the chamber formed by the mask over the nose and mouth of a patient airtight.

Figure 2:
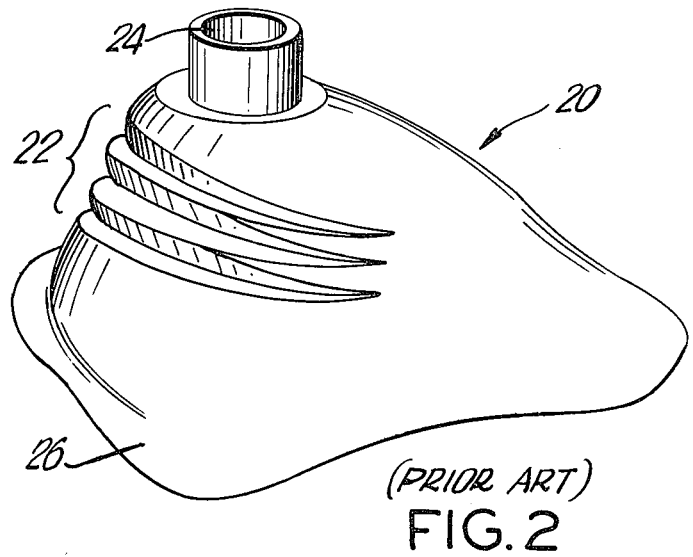
FIG. 2 is a perspective view of a prior art disposable mask.

FIG. 2 shows a prior art disposable mask having a relatively rigid body 20 and formed with an accordion-like section 22 for giving the body some resilience and compliance. The gas inlet 24 is formed in the same manner as the gas inlet 12 of the mask of FIG. 1 and the lip area 26 is formed in somewhat the same shape of the device of FIG. 1 but without the cushioned periphery. The disposable mask of FIG. 2 is generally made of plastic or hard rubber and has a thickness approximately equal to that of a heavy sheet of paper.

Disposable masks of the type shown in FIG. 2 are difficult to work with during long operative procedures and do not form a desirable level of compliance with the face of a patient undergoing an operation. Furthermore, such disposable masks are relatively costly items.

Figure 3:
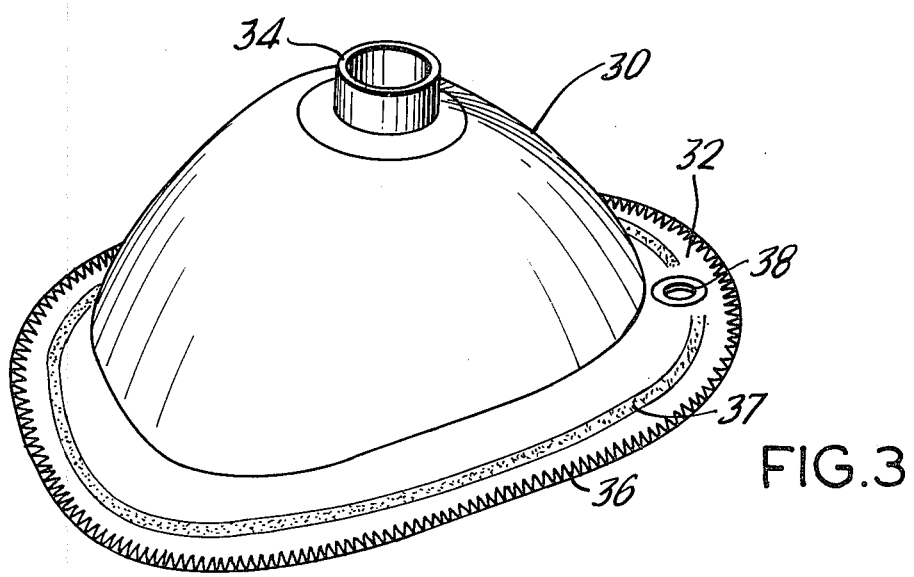
FIG. 3 is a perspective view of a disposable anesthesia mask cover according to the present invention.

Referring now to FIG. 3, a disposable anesthesia mask cover according to the present invention shown in perspective view. The mask cover comprises a composite construction of a relatively rigid inner conical portion 30 and a surrounding pliable, compliant portion 32. At the apex of the generally conical form 30 a cylindrical projection 34 is provided and sized with an outside diameter which will frictionally engage within the inside diameter 12 (FIG. 1) of an existing anesthesia gas mask. The outer pliable, compliant portion 32 of the cover is sized and arranged to engage over the cushioned lip 16 (FIG. 1) of an existing gas mask so as to completely insulate the face of a patient from the material forming the inside and lips of the existing mask.

The projection 34 may comprise a rigid material such as plastic or hard rubber while the somewhat rigid portion 30 may comprise compressed paper covered with a vinyl sheet disposed on the patient's side. This vinyl sheet may extend beyond the periphery of the portion 30 to form the compliant portion 32.

The outer periphery of the compliant portion may be provided with an elastomeric 36 or sticker 37 so as to hold the pliable, compliant portion 32 in an operational posture over the cushioned lips 16 (FIG. 1) of the existing anesthesia gas mask. The compliant portion 32 may further be provided with an opening 38 for receiving the valve 18 (FIG. 1) of an existing anesthesia gas mask which further anchors the compliant pliable portion 32 onto the existing mask body 10.

Figure 4:
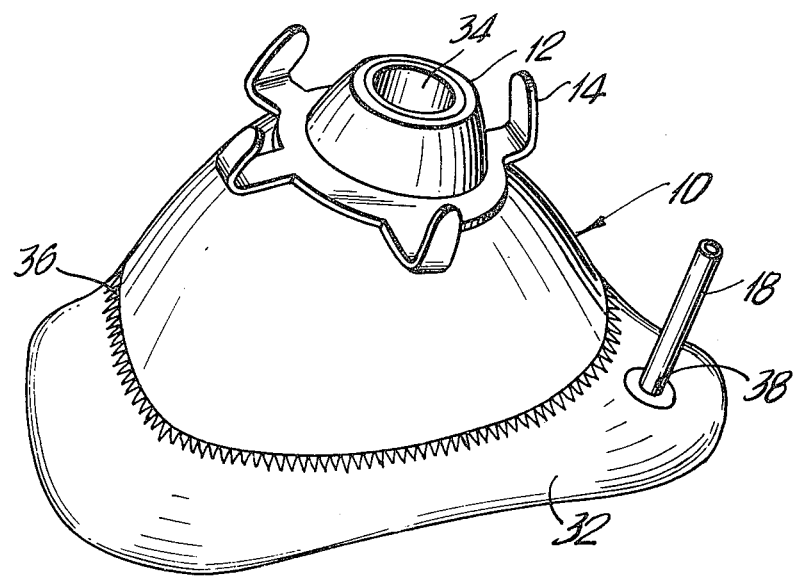
FIG. 4 is a perspective view of a conventional anesthesia mask with a mask cover according to the present invention applied thereto.
Figure 5:
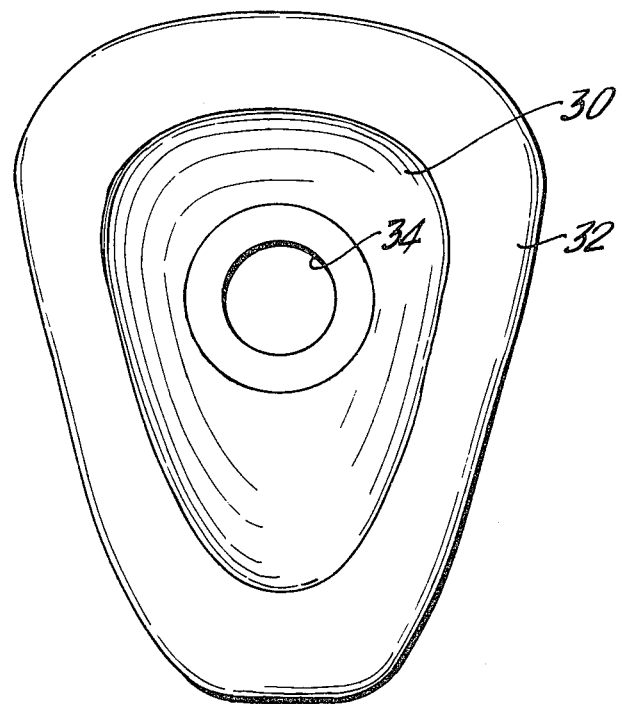
FIG. 5 is another view of the arrangement shown in FIG. 4 looking into the open area of the mask.

Referring to FIGS. 4 and 5, it can be seen that the relatively rigid inner conical portion 30 of the composite mask cover is engaged within the inside of the mask by the frictional engagement of the cylindrical projection 34 within the gas inlet opening 12 of the existing mask 10.

With the inner rigid portion then securely engaged and thus held within the mask, the pliable compliant portion 32 is pulled over the cushioned lip periphery 16 of the mask and the elastomeric 36 holds the compliant pliable portion 32 in place with the valve 18 extending through the opening 38 formed in the cover.

It can thus be seen that a disposable cover has been herein provided for anesthesia gas masks which eliminates the necessity for cleaning or sterilizing a mask after use.

Because the mask need not be cleaned, the mask need not be disconnected from the anesthesia apparatus and a fewer number of masks are required without any increase in the possibility of contamination or in transmitting infection.

Because of the disposable mask as herein described, the anesthesia gas masks need not be brought in contact with special cleaning solutions or gas sterilization materials which may deteriorate the rubber material of the mask requiring expensive replacements.

While what has been described herein is a preferred embodiment of the present invention, it is of course to be understood that various modifications and changes may be made therein without departing from the invention. It is therefore intended to cover in the following claims all such modifications and changes as may fall within the true scope and spirit of the present invention.

What is claimed is:

1. A disposable cover adapted to be inserted within an anesthesia mask having a body portion with a peripheral edge and a central circular inlet opening, said cover comprising a composite member having a pliable peripheral portion surrounding a central more rigid portion, said pliable portion adapted to overlap the peripheral edge of said mask, said more rigid portion being shaped to conform to the inside surface of the body portion of said mask and having tubular projection means alignable with said inlet opening and sized with an outside diameter to be frictionally engaged in said inlet opening and thereby hold said cover within said anesthesia gas mask.

2. A disposable cover for an anesthesia mask according to claim 1 having an elastomeric periphery surrounding said pliable portion thereof for holding said pliable portion in an operational posture over the peripheral edge of the anesthesia mask.

3. A disposable cover for an anesthesia mask according to claim 1 having a sticker means for holding said pliable portion in an operational posture over the peripheral edge of the anesthesia mask.

4. A disposable cover for an anesthesia mask as described in claim 2 which further includes an inflatable peripheral edge with a valve member projecting from the outside surface thereof, said cover further having an opening positioned in said pliable portion and sized to recieve the valve member projecting from the outside surface of said anesthesia mask.

5. A disposable cover for an anesthesia mask as described in claim 3 which further includes an inflatable peripheral edge with a valve member projecting from the outside surface thereof, said cover further having an opening positioned in said pliable portion and sized to receive the valve member projecting from the outside surface of said anesthesia mask.

* * * * *